US008173385B2

(12) United States Patent
Aoyama et al.

(10) Patent No.: US 8,173,385 B2
(45) Date of Patent: May 8, 2012

(54) METHOD FOR STABILIZATION OF PEPTIDES IN A BIOLOGICAL SAMPLE

(75) Inventors: Norihito Aoyama, Gotemba (JP); Kazuhiko Sasaki, Tokyo (JP); Osamu Kusada, Shizuoka (JP)

(73) Assignee: Kyowa Medex Co., Ltd., Tokyo (JP)

( * ) Notice: Subject to any disclaimer, the term of this patent is extended or adjusted under 35 U.S.C. 154(b) by 1144 days.

(21) Appl. No.: 11/994,543

(22) PCT Filed: Jul. 20, 2006

(86) PCT No.: PCT/JP2006/314416
§ 371 (c)(1),
(2), (4) Date: Jan. 3, 2008

(87) PCT Pub. No.: WO2007/010995
PCT Pub. Date: Jan. 25, 2007

(65) Prior Publication Data
US 2009/0035803 A1    Feb. 5, 2009

(30) Foreign Application Priority Data
Jul. 20, 2005    (JP) .................................. 2005-210007

(51) Int. Cl.
G01N 31/00    (2006.01)
C12N 9/00    (2006.01)
C12N 9/99    (2006.01)

(52) U.S. Cl. ................ 435/18; 436/8; 436/15; 435/183; 435/184

(58) Field of Classification Search .......................... None
See application file for complete search history.

(56) References Cited

U.S. PATENT DOCUMENTS

| | | | | |
|---|---|---|---|---|
| 4,040,785 A | * | 8/1977 | Kim et al. | 436/176 |
| 5,547,873 A | * | 8/1996 | Magneson et al. | 436/18 |
| 5,563,122 A | | 10/1996 | Endo et al. | |
| 2003/0036638 A1 | | 2/2003 | Joergensen et al. | |

FOREIGN PATENT DOCUMENTS

| | | |
|---|---|---|
| EP | 267015 A2 * | 5/1988 |
| JP | 63-243756 | 10/1988 |
| JP | 05-170664 | 7/1993 |
| JP | 05-306235 | 11/1993 |
| JP | 06-321800 | 11/1994 |
| JP | 09-208485 | 8/1997 |
| JP | 10-038883 | 2/1998 |
| JP | 10038883 A * | 2/1998 |
| JP | 2002-508843 | 3/2002 |
| JP | 2003-215127 | 7/2003 |
| WO | 98/58259 | 12/1998 |
| WO | 03/092731 | 11/2003 |

OTHER PUBLICATIONS

Pristoupil T., Ulrych S. and Kramlova, M., Study of Hemoglobin Stabilization During Lyophilization with Saccharides, 1980 Collection of Czechoslovakian Chemical Communications, vol. 45, 2583-2586.*
Clark, et al., "Substance P: Correlation of CSF and Plasma Levels", Headache, vol. 34, No. 5 (1994) 261-64.
Cleugh and Gaddaum are the authors, Plattner, et al., "The Stability of Purified Preparations of Substance P", Experientia, vol. 19, No. 2 (1963) 72-3.
Horsthemke, et al, "Degradation of Substance P By Nuerons and Glial Cells", Biochemical and Biophysical Research Communications, vol. 125, No. 2, (1984) 728-33.
Fehder, et al, "Development and Evaluation of a Chromatographic Procedure for Partial Purifications of Substance P with . . . ", Clinical and Diagnostic Laboratory Immunology, vol. 5, No. 3 (1998) 303-07.

* cited by examiner

*Primary Examiner* — Blaine Lankford, Jr
*Assistant Examiner* — Charles Z Constantine
(74) *Attorney, Agent, or Firm* — Fitzpatrick, Cella, Harper & Scinto

(57) ABSTRACT

The present invention provides a simple method for the stabilization of a peptide in a biological sample and a reagent for the stabilization, a simple method for the preservation of a biological sample comprising a peptide and a reagent for the preservation, and a method for the accurate measurement of a peptide in a biological sample and a reagent for the measurement. Addition of a saccharide to a biological sample enables the stabilization of a peptide in the biological sample, the preservation of the biological sample comprising a peptide in a stable condition and the accurate measurement of a peptide in the biological sample. As the present invention can stabilize a peptide in a biological sample collected in the clinical examination, the peptide as a marker in the biological sample can be measured accurately in the clinical examination.

15 Claims, No Drawings

METHOD FOR STABILIZATION OF PEPTIDES IN A BIOLOGICAL SAMPLE

This application is a 371 of PCT Application No. PCT/JP2006/314416 filed Jul. 20, 2006.

TECHNICAL FIELD

The present invention relates to a simple method for the stabilization of a peptide in a biological sample and a reagent for the stabilization, a simple method for the preservation of a biological sample comprising a peptide and a reagent for the preservation, and a method for the accurate measurement of a peptide in a biological sample and a reagent for the measurement.

BACKGROUND ART

Known methods for the stabilization of peptides in a solution include a method which comprises allowing a peptide to stand in a solution containing ethylenediaminetetraacetic acid to form an insoluble composition (see patent document No. 1) and a method which comprises allowing plasma or a protein such as γ-globulin or gelatin to be present with a peptide (see non-patent document No. 1).

A known method for the stabilization of freeze-dried peptides is a method which comprises allowing gluconate to be present with a peptide (see patent document No. 2). Saccharides such as sucrose, maltose and lactose are known as stabilizers of freeze-dried peptides (see patent documents Nos. 3 and 4).

Also, in immunoassay, there is known a method for the stabilization of an antigen or antibody immobilized on a solid phase by allowing saccharides such as trehalose and sucrose to be present (see patent documents Nos. 5 and 6).

In general, peptides in a biological sample are unstable due to various factors (e.g., degradation by protease in the biological sample). For the stabilization of peptides in a biological sample, there are known methods which comprise adding a protease inhibitor, a surfactant or an antiseptic. For example, a method in which protease inhibitors (diisopropyl fluorophosphate and phosphoramidon) and bacitracin are allowed to be present is known as a method for the stabilization of substance P in a biological sample (see non-patent document No. 2).

As to the measurement of substance P in a biological sample, known is a method which comprises treating serum with an acid, extracting substance P with acetone and ether, further purifying it by HPLC using a reversed-phase column, and then measuring substance P by enzyme immunoassay (see non-patent document No. 3). However, this method fails to give accurate measurements because the operations are very complicated and chemical treatment conditions are severe.

Peptides in vivo are important as various kinds of markers and their concentrations in biological samples need to be measured accurately. However, there is the problem that in many cases, peptides in collected biological samples have already decreased at the time of measurement, which makes the accurate measurement difficult.

Patent Document No. 1:
Japanese Published Unexamined Patent Application No. 208485/97
Patent Document No. 2:
Japanese Published Unexamined Patent Application No. 321800/94
Patent Document No. 3:
Japanese Published Unexamined Patent Application No. 306235/93
Patent Document No. 4:
Japanese Published Unexamined Patent Application No. 170664/93
Patent Document No. 5:
PCT National Publication No. 508843/02
Patent Document No. 6:
Japanese Published Unexamined Patent Application No. 215127/03
Non-Patent Document No. 1:
Experientia, Vol. 19, No. 2, p. 72-73, Switzerland (1963)
Non-Patent Document No. 2:
Biochemical and Biophysical Research Communications, Vol. 125, No. 2, P. 728-733, U.S.A. (1984)
Non-Patent Document No. 3:
Clinical and Diagnostic Laboratory Immunology, Vol. 5, No. 3, p. 303-307, U.S.A. (1998)

DISCLOSURE OF THE INVENTION

Problems to be Solved by the Invention

An object of the present invention is to provide a simple method for the stabilization of a peptide in a biological sample and a reagent for the stabilization, a simple method for the preservation of a biological sample comprising a peptide and a reagent for the preservation, and a method for the accurate measurement of a peptide in a biological sample and a reagent for the measurement.

Means for Solving the Problems

The present inventors made intensive studies on a simple method for the stabilization of a peptide in a biological sample. As a result, they have found that a peptide can be stabilized by adding a saccharide to the biological sample and have completed the present invention. That is, the present invention relates to the following [1] to [22].

[1] A method for the stabilization of a peptide in a biological sample, which comprises adding a saccharide to the biological sample comprising the peptide.

[2] A method for the preservation of a biological sample comprising a peptide, which comprises adding a saccharide to the biological sample.

[3] A method for the measurement of a peptide in a biological sample, which comprises using a sample prepared by adding a saccharide to the biological sample comprising the peptide as a sample for the measurement.

[4] The method according to any of [1] to [3], wherein the biological sample is a sample selected from the group consisting of whole blood, serum, plasma, tear fluid, nasal discharge, saliva, urine, feces, spinal fluid, cell, cell tissue fluid and cell membrane.

[5] The method according to any of [1] to [4], wherein the saccharide is a monosaccharide, a disaccharide or a polysaccharide.

[6] The method according to [5], wherein the monosaccharide is hexose.

[7] The method according to [6], wherein the hexose is mannose or galactose.

[8] The method according to [5], wherein the disaccharide is a reducing disaccharide.

[9] The method according to [8], wherein the reducing disaccharide is maltose or lactose.

[10] The method according to [5], wherein the polysaccharide is amylose, cellulose, dextran or starch.
[11] The method according to any of [1] to [10], wherein the peptide is substance P.
[12] A reagent for the stabilization of a peptide in a biological sample, which comprises a saccharide.
[13] A reagent for the preservation of a biological sample comprising a peptide, which comprises a saccharide.
[14] A reagent for the measurement of a peptide in a biological sample, which comprises a saccharide.
[15] The reagent according to any of [12] to [14], wherein the biological sample is a sample selected from the group consisting of whole blood, serum, plasma, tear fluid, nasal discharge, saliva, urine, feces, spinal fluid, cell, cell tissue fluid and cell membrane.
[16] The reagent according to any of [12] to [15], wherein the saccharide is a monosaccharide, a disaccharide or a polysaccharide.
[17] The reagent according to [16], wherein the monosaccharide is hexose.
[18] The reagent according to [17], wherein the hexose is mannose or galactose.
[19] The reagent according to [16], wherein the disaccharide is a reducing disaccharide.
[20] The reagent according to [19], wherein the reducing disaccharide is maltose or lactose.
[21] The reagent according to [16], wherein the polysaccharide is amylose, cellulose, dextran or starch.
[22] The reagent according to any of [12] to [21], wherein the peptide is substance P.

Effect of the Invention

The present invention provides a simple method for the stabilization of a peptide in a biological sample and a reagent for the stabilization, a simple method for the preservation of a biological sample comprising a peptide and a reagent for the preservation, and a method for the accurate measurement of a peptide in a biological sample and a reagent for the measurement.

BEST MODES FOR CARRYING OUT THE INVENTION (1) Peptides

The peptides in the present invention may be any peptides existing in vivo and include those in which a carboxy group at the C terminus is amidated. The number of amino acid residues is preferably 5 to 100, more preferably 5 to 50, and particularly preferably 10 to 30. Preferred are peptides which are measured for the purpose of clinical examination, for example, substance P, calcitonin, somatostatin, calcitonin gene-related peptide, growth hormone-releasing factor, endothelin, endorphin, glucagon, glucagon-like peptide, adrenocorticotropic hormone, corticotropin-releasing factor, vasopressin, luteinizing hormone-releasing hormone, gastrin, parathyroid hormone, natriuretic peptide, secretin, insulin and osteocalcin, among which substance P is favorable.

(2) Biological Samples

Examples of the biological samples in the present invention include whole blood, serum, plasma, tear fluid, nasal discharge, saliva, urine, feces, spinal fluid, cell, cell tissue fluid and cell membrane, and preferred are whole blood, serum, plasma, tear fluid and nasal discharge.

(3) Saccharides

There is no specific restriction as to the saccharides in the present invention as long as they are saccharides enabling the method for the stabilization of a peptide of the present invention to be carried out. Examples of the saccharides include monosaccharides, disaccharides and polysaccharides.

Examples of the monosaccharides include pentose and hexose, and preferred is hexose. Examples of the pentose are arabinose, xylose, ribose, lyxose, ribulose and xylulose. Examples of the hexose are galactose, glucose, talose, mannose, sorbose, tagatose, fructose and psicose, and preferred are mannose and galactose.

Examples of the disaccharides include reducing disaccharides and nonreducing disaccharides, and preferred are reducing disaccharides. Examples of the reducing disaccharides are maltose and lactose, and examples of the nonreducing disaccharides are sucrose and trehalose.

Examples of the polysaccharides are amylose, cellulose, dextran and starch, and preferred is cellulose.

(4) The Method for the Stabilization of a Peptide in a Biological Sample, the Method for the Preservation of a Biological Sample Comprising a Peptide and the Method for the Measurement of a Peptide in a Biological Sample A peptide in a biological sample can be stabilized by adding the above saccharide to the biological sample. The addition of the above saccharide to a biological sample enables the preservation of the biological sample comprising a peptide in a stable condition. Further, the accurate measurement of a peptide in a biological sample becomes possible by using, as a sample for the measurement, a sample prepared by adding the above saccharide to the biological sample because the peptide in the biological sample is kept stable. The saccharide to be added may be one kind or two or more kinds of saccharides. A biological sample is preferably a fresh one, and it is preferable that the saccharide is added immediately or as soon as possible after the biological sample is collected. It is further preferred that the saccharide is previously put in a container to put the collected biological sample in. The saccharide can be added to the biological sample as a solid and dissolved therein, but is preferably added in the form of a solution.

In the method for the stabilization of a peptide in a biological sample, the method for the preservation of a biological sample comprising a peptide and the method for the measurement of a peptide in a biological sample of the present invention, the saccharide is added to the biological sample in an amount to give a concentration such that the peptide can be preserved stably in the biological sample after the addition of the saccharide. When a monosaccharide is used as the saccharide, the concentration of the monosaccharide in the biological sample after the addition of the monosaccharide is, for example, 5 to 600 mg/mL, preferably 10 to 500 mg/mL. When a disaccharide is used as the saccharide, the concentration of the disaccharide in the biological sample after the addition of the disaccharide is, for example, 5 to 600 mg/mL, preferably 10 to 500 mg/mL. When a polysaccharide is used as the saccharide, the concentration of the polysaccharide in the biological sample after the addition of the polysaccharide is, for example, 0.1 to 50 mg/mL, preferably 1 to 20 mg/mL.

In the method for the measurement of a peptide of the present invention, the measurement of a peptide in a sample for the measurement, that is, a biological sample containing an added saccharide, can be carried out, for example, by immunoassay using an antibody specifically binding to the peptide. Examples of immunoassays are sandwich assay and competitive assay. A commercially available kit for the measurement by immunoassay can also be used.

(5) The Reagent for the Stabilization of a Peptide in a Biological Sample, the Reagent for the Preservation of a Biological Sample Comprising a Peptide and the Reagent for the Measurement of a Peptide in a Biological Sample The reagent for the stabilization of a peptide in a biological sample, the reagent for the preservation of a biological sample comprising a peptide and the reagent for the measurement of a peptide in a biological sample of the present invention comprise a saccharide. The reagent for the stabilization, the reagent for the preservation and the reagent for the measurement of the present invention may be in the form of a freeze-dried product or a liquid. Further, the reagent for the measurement of the present invention may take the form of a kit, which is a form suitable for transportation and preservation. A kit may be composed of two reagents, three reagents or the like. Examples of the saccharides include the saccharides described in the above (3). The saccharide may be one kind or two or more kinds of saccharides.

In one embodiment of use of the reagent for the stabilization, the reagent for the preservation and the reagent for the measurement of the present invention, the reagent for the stabilization, the reagent for the preservation and the reagent for the measurement of the present invention are allowed to be previously present in an apparatus for collecting a biological sample. In this embodiment, a peptide can be immediately stabilized in the collected biological sample. An example of such an apparatus for collecting a biological sample is a vacuum blood-collecting tube. A sample obtained by adding a biological sample to the reagent for the measurement of the present invention contained in the apparatus is subjected to the measurement as a sample for the measurement, as such or after being appropriately dissolved in an aqueous medium such as a buffer, or being concentrated or diluted.

The reagent for the stabilization, the reagent for the preservation and the reagent for the measurement of the present invention may comprise a chelating agent, an antiseptic, a surfactant, a buffer, a protease inhibitor, a salt, etc. according to need. Examples of the chelating agents include ethylenediaminetetraacetic acid (EDTA) or its salt, diphenyldithiocarbazone (DZ), 8-quinolinol (OX) and 6-dodecyl-4-(2-thiazolylazo)resorcinol (DTAR). An example of the salt of ethylenediaminetetraacetic acid is ethylenediaminetetraacetic acid.disodium (EDTA.2Na). Examples of the antiseptics are sodium azide, streptomycin sulfate, paraoxybenzoic acid esters and ethylene glycol monophenyl ether. Examples of the salts are sodium chloride and potassium chloride.

Examples of the surfactants include anionic surfactants, nonionic surfactants, amphoteric surfactants and cationic surfactants.

Examples of the anionic surfactants are fatty acid anionic surfactants (e.g., alpha-sulfo-fatty acid ester sodium salt), alkylbenzene anionic surfactants (e.g., sodium alkylbenzene sulfonate), alkyl sulfate anionic surfactants (e.g., sodium alkyl sulfate and sodium alkyl ether sulfate), alpha olefin anionic surfactants (e.g., sodium alpha olefin sulfonate) and alkylsulfonic acid anionic surfactants (e.g., sodium alkylsulfonate).

Examples of the nonioic surfactants are fatty acid nonionic surfactants (e.g., sorbitan fatty acid ester and polyoxyethylene sorbitan fatty acid ester), alkyl ether nonionic surfactants (e.g., polyoxyethylene alkyl ether) and alkylphenol nonionic surfactants (e.g., polyoxyethylene alkylphenyl ether).

Examples of the amphoteric surfactants are amino acid amphoteric surfactants (e.g., alkylamino fatty acid sodium salt), betaine amphoteric surfactants (e.g., alkyl betaine) and amine oxide amphoteric surfactants (e.g., alkylamine oxide).

Examples of the cationic surfactants are quaternary ammonium salt cationic surfactants such as alkyl trimethyl ammonium salt and dialkyl dimethyl ammonium salt.

Examples of the buffer are lactate buffer, citrate buffer, acetate buffer, succinate buffer, glycine buffer, 3,3-dimethyl glutarate buffer, phthalate buffer, phosphate buffer, triethanolamine buffer, diethanolamine buffer, borate buffer, barbiturate buffer, tris(hydroxymethyl)aminomethane buffer, imidazole acetate buffer, malate buffer, oxalate buffer, carbonate buffer, lysine buffer and Good's buffer.

Examples of Good's buffers include Tris [tris(hydroxymethyl)aminomethane] buffer, MES (2-morpholinoethanesulfonic acid) buffer, Bis-Tris [bis(2-hydroxyethyl)iminotris (hydroxymethyl)methane] buffer, ADA [N-(2-acetamido) iminodiacetic acid] buffer, PIPES [piperazine-N,N'-bis(2-ethanesulfonic acid)] buffer, ACES {2-[N-(2-acetamido) amino]ethanesulfonic acid} buffer, MOPSO (3-morpholino-2-hydroxypropanesulfonic acid) buffer, BES {2-[N,N-bis(2-hydroxyethyl)amino]ethanesulfonic acid} buffer, MOPS (3-morpholinopropanesulfonic acid) buffer, TES <2-{N-[tris (hydroxymethyl)methyl]amino}ethanesulfonic acid> buffer, HEPES [N-(2-hydroxyethyl)-N'-(2-sulfoethyl)piperazine] buffer, DIPSO {3-[N,N-bis(2-hydroxyethyl)amino]-2-hydroxypropanesulfonic acid} buffer, TAPSO <2-hydroxy-3-{[N-tris(hydroxymethyl)methyl]amino}propanesulfonic acid> buffer, POPSO [piperazine-N,N'-bis(2-hydroxypropane-3-sulfonic acid)] buffer, HEPPSO [N-(2-hydroxyethyl)-N'-(2-hydroxy-3-sulfopropyl)piperazine] buffer, EPPS [N-(2-hydroxyethyl)-N'-(3-sulfopropyl)piperazine] buffer, Tricine [N-tris(hydroxymethyl)methylglycine] buffer, Bicine [N,N-bis(2-hydroxyethyl)glycine] buffer, TAPS {3-[N-tris(hydroxymethyl)methyl]aminopropanesulfonic acid} buffer, CHES [2-(N-cyclohexylamino)ethanesulfonic acid] buffer, CAPSO [3-(N-cyclohexylamino)-2-hydroxypropanesulfonic acid] buffer and CAPS [3-(N-cyclohexylamino)propanesulfonic acid] buffer.

Examples of the protease inhibitors include aprotinin, gabexate, tranexamic acid, diisopropylfluorophosphate, phosphoramidon and bacitracin.

Certain embodiments of the present invention are illustrated in the following examples. These examples are not to be construed as limiting the scope of the present invention. Apparatus and reagents used in the examples are products from the following manufacturers. Vacuum blood-collecting tube containing EDTA.2Na and aprotinin (Nipro Corporation), xylose (special grade; Wako Pure Chemical Industries, Ltd.), glucose (special grade; Kanto Chemical Co., Inc.), mannose (special grade; Wako Pure Chemical Industries, Ltd.), galactose (special grade; Nacalai Tesque, Inc.), maltose (special grade; Wako Pure Chemical Industries, Ltd.), sucrose (special grade; Kanto Chemical Co., Inc.), lactose (special grade; Nacalai Tesque, Inc.), trehalose (Nihon Shokuhin Kako Co., Ltd.), amylose (Wako Pure Chemical Industries, Ltd.), cellulose (Nacalai Tesque, Inc.), dextran (special grade; Wako Pure Chemical Industries, Ltd.), starch (soluble; Kanto Chemical Co., Inc.), ethylenediaminetetraacetic acid-disodium (EDTA2Na) (Dojindo Laboratories), potassium gluconate (special grade; Wako Pure Chemical Industries, Ltd.), sodium gluconate (special grade; Wako Pure Chemical Industries, Ltd.), magnesium gluconate hydrate (Wako Pure Chemical Industries, Ltd.), phosphoramidon (SIGMA) and neutral endopeptidase (NEP) (Erastin Products).

Example 1

Stabilization of Substance P in Plasma by Addition of Monosaccharides (1) Preparation of Samples for the Measurement and a Control Sample Blood was collected from a human donor using a vacuum blood-collecting tube containing EDTA.2Na and aprotinin and fresh human plasma was prepared within 3 hours. To 50 µL portions of the human plasma were respectively added a 200 mg/mL aqueous solution of xylose, a 200 mg/mL aqueous solution of glucose, a 200 mg/mL aqueous solution of mannose and a 200 mg/mL aqueous solution of galactose (100 µL each), followed by mixing. Then, to the resulting mixtures was added a 200 pg/mL aqueous solution of substance P (50 µL) to prepare samples A to D. The aqueous solutions of monosaccharides were prepared with purified water. Separately, to a 50 µL portion of the human plasma was added a 200 pg/mL aqueous solution of substance P (50 µL) to prepare a control sample.

(2) Preparation of a Calibration Curve and Measurement of the Concentration of Substance P in Each Sample Measurement of substance P in samples A to D and the control sample was carried out in duplicate in the following manner, using Substance P EIA Kit (Cayman) according to the manual attached to the kit.

The above kit is a kit for enzyme immunoassay by the competitive method using, as a competitive substance, substance P bound to acetylcholine esterase (substance P AchE tracer). The measurement with this kit is carried out by allowing substance P in a sample and the competitive substance to competitively react with anti-substance P antibody on a solid phase and reacting acetylcholine esterase in the competitive substance bound to the anti-substance P antibody on a solid phase with Ellman's reagent to develop color, followed by the measurement of the absorbance. Then, the concentration of substance P in the sample can be determined based on a previously prepared calibration curve.

First, the following were prepared using reagents in the kit: EIA buffer, wash buffer, substance P AchE tracer, substance P antiserum, Ellman's reagent and standard solutions 1 to 8 respectively having substance P concentrations of 500 pg/mL, 250 pg/mL, 125 pg/mL, 62.5 pg/mL, 31.2 pg/mL, 15.6 pg/mL, 7.8 pg/mL and 3.9 pg/mL. Ellman's reagent was prepared just before the completion of overnight incubation in the following method for the measurement. Using these reagents for the measurement, a calibration curve was prepared which indicates the relationship between the concentration of substance P and the index (% $B/B_0$) related to the amount of the competitive substance bound to a solid phase which was calculated from the absorbance as described below. The measurement of samples A to D and the control sample was also carried out.

The following reaction wells (a) to (f) were set on a 96-well ELISA plate previously adjusted to room temperature, and the following solutions were put into the respective wells: (a) blank; no addition: (b) total activity; no addition: (c) non-specific binding; 100 µL of EIA buffer and 50 µL of substance P AchE tracer: (d) maximum binding; 50 µL of EIA buffer, 50 µL of substance P AchE tracer and 50 µL of substance P antiserum: (e) standard solutions 1 to 8; 50 µL of each of the above standard solutions 1 to 8, 50 µL of substance P AchE tracer and 50 µL of substance P antiserum: and (f) sample; 50 µL of each of the samples for the measurement (samples A to D or the control sample), 50 µL of substance P AchE tracer and 50 µL of substance P antiserum.

The 96-well plate was covered with a plastic film attached to the kit and incubated at 4° C. for 18 hours. After the incubation, the plate was washed 5 times with the wash buffer (250 µL/reaction well) using a plate washer (model 1575 ImmunoWash, Bio-Rad). After confirming that no wash buffer was remaining in the reaction wells, 200 µL of Ellman's reagent was put therein, followed by further addition of substance P AchE tracer (5 µL) only to the total activity well. The resulting plate was shaded and incubated at 25° C. for 2 hours. After the incubation, the absorbance was measured at a wavelength of 405 nm with a plate reader (MTP-120 micro plate reader, Corona Corporation).

The average of the absorbance values for each of the standard solutions 1 to 8 in the respective reaction wells was designated as B, the average of the absorbance values of the reaction wells of maximum binding was designated as $B_0$, and the average of the absorbance values of the reaction wells of non-specific binding was designated as NSB. The value (% $B/B_0$) represented by the following equation was calculated with respect to the standard solutions 1 to 8, respectively, and the concentration of substance P and the values of % $B/B_0$ were plotted to prepare a calibration curve.

$$\% B/B_0 = [(B-NSB)/(B_0-NSB)] \times 100$$

The value of % $B/B_0$ for each sample was calculated from the absorbance in the same manner. With respect to B, the absorbance of the respective well was used in place of the average value of the duplicate experiment. The concentration of substance P was calculated from the calibration curve obtained above based on % $B/B_0$ of each sample and the obtained value was used as the measurement value for each sample.

(3) Stabilization of Substance P in Samples for the Measurement

The 200 pg/mL aqueous solution of substance P and the human plasma used for the preparation of the above samples for the measurement were used as samples for the measurement, and substance P in the respective samples was measured using Substance P EIA Kit (Cayman) by the above method. As a result, the concentrations of substance P in the 200 pg/mL aqueous solution of substance P and the human plasma were determined to be 226.16 pg/mL and 7.70 pg/mL, respectively. From the respective measurement values, the theoretical values of substance P in the control sample and samples A to D were calculated according to the following equations.

Theoretical value of the concentration of substance $P$ in the control sample=(measurement value of the aqueous solution of substance $P \times 50$ + measurement value of the human plasma $\times 50$)/100

Theoretical value of the concentration of substance $P$ in samples $A$ to $D$=(measurement value of the aqueous solution of substance $P \times 50$ + measurement value of the human plasma $\times 50$)/200

The residual rate was calculated from the theoretical value and the measurement value of each sample according to the following equation and the obtained value was made an index for the stability of substance P in plasma.

Residual rate=(average of the measurement values of substance $P$/theoretical value of substance $P$) $\times 100$ The theoretical value, the measurement values and the residual rate of each sample are shown in Table 1.

TABLE 1

| | | Substance P concentration (pg/mL) | | | | |
|---|---|---|---|---|---|---|
| Sample | Saccharide | Theoretical value | Measurement value 1 | Measurement value 2 | Average value | Residual rate (%) |
| Control | — | 116.93 | 59.9 | 61.3 | 60.57 | 51.8 |
| A | Xylose | 58.46 | 37.1 | 33.3 | 35.23 | 60.3 |
| B | Glucose | 58.46 | 39.0 | 41.1 | 40.07 | 68.5 |
| C | Mannose | 58.46 | 48.1 | 50.0 | 49.07 | 83.9 |
| D | Galactose | 58.46 | 43.1 | 48.3 | 45.74 | 78.2 |

When the 200 pg/mL aqueous solution of substance P was, without being mixed with the human plasma, subjected to measurement of substance P under the present measurement conditions including incubation at 4° C. for 18 hours, the obtained value was 226.16 pg/mL. This result shows that substance P in the aqueous solution was stable. On the other hand, as shown in the experiment on the control sample, when the sample having the initial substance P concentration of 116.93 pg/mL was subjected to measurement under the present measurement conditions including incubation at 4° C. for 18 hours, the obtained average substance P concentration was 60.57 pg/mL. This result shows that substance P was unstable in the presence of plasma.

The residual rates of substance P in the samples to which the monosaccharides were added were as follows, whereas that of the control was 51.8%: sample A (addition of xylose), 60.3%; sample B (addition of glucose), 68.5%; sample C (addition of mannose), 83.9%; and sample D (addition of galactose), 78.2%. It was thus revealed that substance P in plasma is stabilized by addition of a monosaccharide. Specifically, in the samples to which hexoses (glucose, mannose and galactose) were added, substance P was significantly ($P<0.05$) stabilized compared with that in the control sample, showing that hexose is more useful for the stabilization of substance P in plasma. As the hexose, mannose and galactose showed a higher effect on the stabilization of substance P.

Example 2

Stabilization of Substance P in Plasma by Addition of Disaccharides

To 50 μL portions of human plasma prepared in the same manner as in Example 1 were respectively added a 100 mg/mL aqueous solution of maltose, a 100 mg/mL aqueous solution of sucrose, a 100 mg/mL aqueous solution of lactose and a 100 mg/mL aqueous solution of trehalose (100 μL each), followed by mixing. Then, to the resulting mixtures was added a 200 pg/mL aqueous solution of substance P (50 μL) to prepare samples E to H. The aqueous solutions of disaccharides were prepared with purified water. Separately, to a 50 μL portion of the human plasma was added a 200 pg/mL aqueous solution of substance P (50 μL) to prepare a control sample.

Immediately after the preparation of samples E, F, G and H and the control sample, the concentrations of substance P in the respective samples were measured in the same manner as in Example 1 to calculate the residual rates, which are the index for the stability of substance P in plasma. The results are shown in Table 2.

TABLE 2

| | | Substance P concentration (pg/mL) | | | | |
|---|---|---|---|---|---|---|
| Sample | Saccharide | Theoretical value | Measurement value 1 | Measurement value 2 | Average value | Residual rate (%) |
| Control | — | 116.93 | 59.9 | 61.3 | 60.57 | 51.8 |
| E | Maltose | 58.46 | 47.3 | 50.5 | 48.88 | 83.6 |
| F | Sucrose | 58.46 | 41.1 | 44.9 | 43.04 | 73.6 |
| G | Lactose | 58.46 | 51.4 | 43.8 | 47.62 | 81.4 |
| H | Trehalose | 58.46 | 40.2 | 43.5 | 41.84 | 71.6 |

The residual rates of substance P in the samples to which the disaccharides were added were as follows, whereas that of the control was 51.8%: sample E (addition of maltose), 83.6%; sample F (addition of sucrose), 73.6%; sample G (addition of lactose), 81.4%; and sample H (addition of trehalose), 71.6%. In these samples, substance P was significantly ($P<0.05$) stabilized compared with that in the control sample, and it was revealed that substance P in plasma is stabilized by adding a disaccharide to the plasma. Specifically, maltose and lactose were more useful for the stabilization of substance P in plasma.

Example 3

Stabilization of Substance P in Plasma by Addition of Polysaccharides

To 50 μL portions of human plasma prepared in the same manner as in Example 1 were respectively added a 10 mg/mL aqueous solution of amylose, a 10 mg/mL aqueous solution of cellulose, a 10 mg/mL aqueous solution of dextran and a 10 mg/mL aqueous solution of starch (100 μL each), followed by mixing. Then, to the resulting mixtures was added a 200 pg/mL aqueous solution of substance P (50 μL) to prepare samples I to L. The aqueous solutions of polysaccharides were prepared with purified water. Separately, to a 50 μL portion of the human plasma was added a 200 pg/mL aqueous solution of substance P (50 μL) to prepare a control sample.

Immediately after the preparation of samples I, J, K and L and the control sample, the concentrations of substance P in the respective samples were measured in the same manner as in Example 1 to calculate the residual rates, which are the index for the stability of substance P in plasma. The results are shown in Table 3.

TABLE 3

| | | Substance P concentration (pg/mL) | | | | |
|---|---|---|---|---|---|---|
| Sample | Saccharide | Theoretical value | Measurement value 1 | Measurement value 2 | Average value | Residual rate (%) |
| Control | — | 116.93 | 59.9 | 61.3 | 60.57 | 51.8 |
| I | Amylose | 58.46 | 41.8 | 39.3 | 40.54 | 69.3 |
| J | Cellulose | 58.46 | 41.8 | 42.8 | 42.29 | 72.3 |
| K | Dextran | 58.46 | 39.9 | 43.1 | 41.51 | 71.0 |
| L | Starch | 58.46 | 35.0 | 35.5 | 35.27 | 60.3 |

The residual rates of substance P in the samples to which the polysaccharides were added were as follows, whereas that of the control was 51.8%: sample I (addition of amylose), 69.3%; sample J (addition of cellulose), 72.3%; sample K (addition of dextran), 71.0%; and sample L (addition of starch), 60.3%. In these samples, substance P was significantly ($P<0.05$) stabilized compared with that in the control sample, and it was revealed that polysaccharides are useful for the stabilization of substance P in plasma.

Example 4

Stabilization of Substance P in Plasma by Addition of a Saccharide at 4° C.

To 50 μL portions of human plasma prepared in the same manner as in Example 1 was added a 400 mg/mL aqueous solution of glucose (special grade; Kanto Chemical Co., Inc.) prepared with purified water (100 μL), followed by mixing. Then, to the resulting mixture was added a 200 pg/mL aqueous solution of substance P (50 μL) to prepare three portions of sample M. Separately, to 50 μL portions of the human plasma was added a 200 pg/mL aqueous solution of substance P (50 μL) to prepare three portions of control sample.

The concentrations of substance P in the respective samples, and the human plasma and the 200 pg/mL aqueous solution of substance P used for the preparation of the samples were measured in the same manner as in Example 1 to calculate the residual rates, which are the index for the stability of substance P in plasma. The incubation time at 4° C., which was 18 hours in Example 1, was changed to 16 hours, 24 hours and 48 hours in the present experiment.

The concentrations of substance P in the human plasma used for the preparation of the samples subjected to the incubation for 16 hours, 24 hours and 48 hours were determined to be 15.02 pg/mL, 4.95 pg/mL and 5.71 pg/mL, respectively. The concentrations of substance P in the substance P solution used for the preparation of the samples subjected to the incubation for 16 hours, 24 hours and 48 hours were determined to be 211.1 pg/mL, 208.4 pg/mL and 197.8 pg/mL, respectively. From these measurement values, the theoretical values of the concentrations of substance P in the samples were calculated in the same manner as in Example 1, and the residual rates were calculated from the theoretical values and the measurement values. The results are shown in Table 4.

TABLE 4

| | | | Substance P concentration (pg/mL) | | | |
|---|---|---|---|---|---|---|
| Sample | Glucose | Incubation | Theoretical value | Measurement value 1 | Measurement value 2 | Average value | Residual rate |
| Control | − | 16 hours | 108.1 | 86.4 | 87.5 | 86.94 | 80.5 |
| Control | − | 24 hours | 106.7 | 63.6 | 64.0 | 63.78 | 59.8 |
| Control | − | 48 hours | 101.7 | 60.9 | 50.9 | 55.92 | 55.0 |
| M | + | 16 hours | 54.0 | 56.0 | 57.9 | 56.95 | 105.4 |
| M | + | 24 hours | 53.3 | 55.1 | 52.5 | 53.79 | 100.9 |
| M | + | 48 hours | 50.9 | 52.2 | 54.4 | 53.25 | 104.7 |

In the case of the control sample, the residual rate of substance P decreased as the incubation time at 4° C. became longer (16 hours, 24 hours and 48 hours). On the other hand, in the case of the sample to which glucose was added, the residual rates of substance P after incubation for 16 hours, 24 hours and 48 hours were all higher than 100%, and a decrease in the residual rate was not observed. Thus, the saccharide was useful for the stabilization of substance P in the plasma at 4° C.

Example 5

Stabilization of Substance P in Plasma by Addition of a Saccharide when Frozen (1)

To 50 μL portions of human plasma prepared in the same manner as in Example 1 was added a 400 mg/mL aqueous solution of glucose (special grade; Kanto Chemical Co., Inc.) prepared with purified water (100 μL), followed by mixing. Then, to the resulting mixture was added a 200 pg/mL aqueous solution of substance P (50 μL) to prepare three portions of sample N. These portions of sample N were frozen at −80° C. and were respectively thawed at room temperature 0 day (immediately after the preparation), 7 days and 15 days after the freezing. The concentrations of substance P in the thawed portions of sample N were measured in the same manner as in Example 1 to calculate the residual rates, which are the index for the stability of substance P in plasma. The results are shown in Table 5.

TABLE 5

| Sample | Saccharide | Residual rate (%) | | |
|---|---|---|---|---|
| | | Day 0 | Day 7 | Day 15 |
| N | Glucose | 85.8 | 85.8 | 86.4 |

The residual rates of substance P in the portions of sample N containing glucose were 85.8% (after 7 days) and 86.4% (after 15 days), while that immediately after the preparation (0 day) was 85.8%, and a decrease in the residual rate was not observed. Thus, the saccharide was useful for the stabilization of substance P in the plasma even when frozen.

Example 6

Stabilization of Substance P in Plasma by Addition of a Saccharide when Frozen (2)

To 50 µL portions of human plasma prepared in the same manner as in Example 1 was added a 200 pg/mL aqueous solution of substance P (50 µL) to prepare six portions of sample. To these portions were respectively added a 400 mg/mL aqueous solution of glucose, a 2.5 mg/mL aqueous solution of EDTA.2Na, a 60 mg/mL aqueous solution of potassium gluconate, a 40 mg/mL aqueous solution of sodium gluconate, a 50 mg/mL aqueous solution of magnesium gluconate and a 10 mmol/L aqueous solution of phosphoramidon (100 µL each), followed by mixing, to prepare samples O to T. EDTA.2Na and the gluconates are peptide stabilizers respectively described in patent document 1 and patent document 2.

After the preparation, the samples were frozen at −80° C. and then thawed at room temperature 0 day, 3 days and 13 days after the freezing. The concentrations of substance P in the thawed samples were measured in the same manner as in Example 1 using Substance P EIA Kit (Cayman) to calculate the residual rates, which are the index for the stability of substance P in plasma. The results are shown in Table 6.

TABLE 6

| | Sample | Residual rate (%) | | |
|---|---|---|---|---|
| | | Day 0 | Day 3 | Day 13 |
| O | Glucose | 79.8 | 78.5 | 72.3 |
| P | EDTA•2Na | 104.4 | 26.4 | 32.6 |
| Q | Potassium gluconate | 80.0 | 31.4 | 30.1 |
| R | Sodium gluconate | 74.3 | 32.2 | 30.3 |
| S | Magnesium gluconate | 82.9 | 42.6 | 40.1 |
| T | Phosphoramidon | 87.6 | 29.0 | 25.6 |

As shown in Table 6, substance P present in the plasma in a frozen state was significantly stabilized when glucose was added, compared with when EDTA.2Na, various gluconates (potassium gluconate, sodium gluconate and magnesium gluconate) and phosphoramidon were added. It was thus revealed that the method for the stabilization of the present invention is also useful for the stabilization of substance P present in plasma in a frozen state.

Example 7

Effect of Addition of a Saccharide on Degradation of Substance P by Neutral Endopeptidase (NEP)

Samples each comprising 150 µL of human plasma prepared in the same manner as in Example 1, 150 µL of a 200 pg/mL aqueous solution of substance P and 50 µL of an enzyme solution (respective NEP concentrations; 0 U/mL, 0.1 U/mL, 1.0 U/mL and 10.0 U/mL) were prepared.

Similarly, samples each comprising 150 µL of human plasma, 150 µL of a 200 pg/mL aqueous solution of substance P, 300 µL of a 400 mg/mL aqueous solution of glucose and 50 µL of an enzyme solution (respective NEP concentrations; 0 U/mL, 0.1 U/mL, 1.0 U/mL and 10.0 U/mL) were prepared.

Further, samples each comprising 150 µL of human plasma, 150 µL of a 200 pg/mL aqueous solution of substance P, 300 µL of a 10 mmol/L aqueous solution of phosphoramidon and 50 µL of an enzyme solution (respective NEP concentrations; 0 U/mL, 0.1 U/mL, 1.0 U/mL and 10.0 U/mL) were prepared.

The substance P concentration of each sample was measured in the same manner as in Example 1 using Substance P EIA Kit (Cayman) to calculate the residual rate of substance P. The results are shown in Table 7.

TABLE 7

| | Residual rate (%) NEP concentration (U/mL) | | | |
|---|---|---|---|---|
| Sample | 0 | 0.1 | 1.0 | 10.0 |
| Substance P | 100.0 | 102.2 | 93.3 | 84.0 |
| Glucose + substance P | 100.0 | 98.7 | 95.8 | 98.3 |
| Phosphoramidon + substance P | 100.0 | 103.9 | 103.4 | 96.2 |

As can be seen from Table 7, substance P was degraded by NEP and the degradation proceeded in a manner dependent on the NEP concentration, but the degradation of substance P by NEP was inhibited by the addition of glucose or phosphoramidon.

Example 8

Reagent for the Stabilization of Substance P

| Phosphate buffer | 81.5 mmol/L |
|---|---|
| Sodium chloride | 80.0 g/L |
| Potassium chloride | 0.2 g/L |
| EDTA•2Na | 0.09 g/L |
| Sodium azide | 1.0 g/L |
| Glucose | 400.0 g/L |

INDUSTRIAL APPLICABILITY

The present invention provides a method for the stabilization of a peptide in a biological sample. As the method can stabilize, for example, a peptide in a biological sample collected in the clinical examination, the peptide as a marker in the biological sample can be measured accurately in the clinical examination.

The invention claimed is:

1. A method for the measurement of substance P in a biological sample containing neutral endopeptidase, which comprises adding a saccharide to the biological sample in an amount sufficient to stabilize the substance P against degradation by neutral endopeptidase, and measuring the substance P in the sample.

2. The method according to claim 1, wherein the biological sample is selected from the group consisting of whole blood, serum, plasma, tear fluid, nasal discharge, saliva, urine, feces, spinal fluid, cell, cell tissue fluid and cell membrane.

3. The method according to claim 2, wherein the saccharide is a monosaccharide, a disaccharide or a polysaccharide.

4. The method according to claim 2, wherein the saccharide is hexose.

5. The method according to claim 4, wherein said saccharide is added to said biological sample at 10 to 500 mg/mL.

6. The method according to claim 4, wherein said saccharide is added to said biological sample at 5 to 600 mg/mL.

7. The method according to claim 6, wherein the hexose is glucose, mannose or galactose.

8. The method according to claim 6, wherein the hexose is glucose.

9. The method according to claim 2, wherein the saccharide is a reducing disaccharide.

10. The method according to claim 9, wherein said saccharide is added to said biological sample at 10 to 500 mg/mL.

11. The method according to claim 9, wherein said saccharide is added to said biological sample at 5 to 600 mg/mL.

12. The method according to claim 11, wherein the reducing disaccharide is maltose or lactose.

13. The method according to claim 2, wherein the saccharide is amylose, cellulose, dextran or starch.

14. The process method according to claim 13, wherein said saccharide is added to said biological sample at 0.1 to 50 mg/mL.

15. The method according to claim 13, wherein said saccharide is added to said biological sample at 1 to 20 mg/mL.

* * * * *

UNITED STATES PATENT AND TRADEMARK OFFICE
CERTIFICATE OF CORRECTION

| | |
|---|---|
| PATENT NO. | : 8,173,385 B2 |
| APPLICATION NO. | : 11/994543 |
| DATED | : May 8, 2012 |
| INVENTOR(S) | : Norihito Aoyama et al. |

Page 1 of 1

It is certified that error appears in the above-identified patent and that said Letters Patent is hereby corrected as shown below:

COVER PAGE:

References Cited (56):
    FOREIGN PATENT DOCUMENTS, "JP 10038883A * 2/1998" should be deleted
        (duplicate); and
    OTHER PUBLICATIONS, Under Horsthemke, et al. "Nuerons" should read
        --Neurons--.

COLUMN 16:

Line 9, "process" should be deleted.

Signed and Sealed this
Fourteenth Day of August, 2012

David J. Kappos
*Director of the United States Patent and Trademark Office*